(12) United States Patent
Kato et al.

(10) Patent No.: US 8,123,680 B2
(45) Date of Patent: Feb. 28, 2012

(54) ENDOSCOPE

(75) Inventors: Takayuki Kato, Tokyo (JP); Koichiro Ito, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 12/924,318

(22) Filed: Sep. 24, 2010

(65) Prior Publication Data
US 2011/0157574 A1    Jun. 30, 2011

Related U.S. Application Data

(63) Continuation of application No. PCT/JP2010/052300, filed on Feb. 17, 2010.

(30) Foreign Application Priority Data

Mar. 31, 2009   (JP) .................................. 2009-086964

(51) Int. Cl.
*A61B 1/06* (2006.01)
*A61B 1/07* (2006.01)

(52) U.S. Cl. .......................... 600/177; 600/129; 600/182

(58) Field of Classification Search .................. 600/177, 600/176, 129, 182
See application file for complete search history.

(56) References Cited

U.S. PATENT DOCUMENTS

| | | | | |
|---|---|---|---|---|
| 4,266,534 A | * | 5/1981 | Ogawa | 600/177 |
| 4,272,156 A | * | 6/1981 | Ishibashi et al. | 385/117 |
| 5,184,602 A | * | 2/1993 | Anapliotis et al. | 600/137 |
| 7,585,274 B2 | * | 9/2009 | Homma | 600/160 |
| 2001/0003142 A1 | * | 6/2001 | Koshikawa | 600/177 |
| 2007/0038031 A1 | * | 2/2007 | Miyagi et al. | 600/182 |
| 2007/0106120 A1 | * | 5/2007 | Iijima | 600/182 |
| 2007/0118013 A1 | * | 5/2007 | Miyagi et al. | 600/129 |
| 2007/0135682 A1 | * | 6/2007 | Miyagi et al. | 600/129 |
| 2008/0242935 A1 | * | 10/2008 | Inoue | 600/176 |

FOREIGN PATENT DOCUMENTS

| | | |
|---|---|---|
| JP | 60-140021 | 9/1985 |
| JP | 03-287218 | 12/1991 |
| JP | 09-105871 | 4/1997 |
| JP | 09-220192 | 8/1997 |
| JP | 10-033461 | 2/1998 |
| JP | 10-288742 | 10/1998 |
| JP | 2005-074015 | 3/2005 |
| JP | 2006-122498 | 5/2006 |
| JP | 2007-216054 | 8/2007 |

* cited by examiner

*Primary Examiner* — John P Leubecker
(74) *Attorney, Agent, or Firm* — Kenyon & Kenyon LLP (57) ABSTRACT

An endoscope includes an image acquisition device, an objective optical system having a predetermined optical axis, first and second light guiding members that emit first and second illumination light, first and second optical systems that refract the first and second illumination light to intersect with the optical axis of the objective optical system, and a tube-like inserted portion having a distal end. The first and second optical systems are disposed at substantially mirror symmetrical positions at the distal end having a shoulder portion that becomes narrower toward the tip. When viewed from the optical axis direction of the objective optical system, the inclination directions at substantially the center of the outer surfaces of the first and second optical systems and straight lines that pass through the center of the objective optical system and the centers of the first and second optical systems form angles of 30° or less.

4 Claims, 10 Drawing Sheets

INCLINATION-DIRECTION SECTION
R CURVATURE→LARGE

FIG. 5C

INCLINATION-DIRECTION SECTION
R CURVATURE→SMALL

ENDOSCOPE

CROSS REFERENCE TO RELATED APPLICATIONS

This is a continuation of International Application PCT/JP2010/052300, with an international filing date of Feb. 17, 2010, which is hereby incorporated by reference herein in its entirety. This application claims the benefit of Japanese Patent Application No. 2009-086964, the content of which is incorporated herein by reference.

BACKGROUND OF THE INVENTION

1. Field of the Invention

The present invention relates to an endoscope.

2. Description of Related Art

In the related art, endoscopes provided with an image-acquisition device and a light guide for guiding illumination light to the tip of an inserted portion, wherein the light guide is inclined relative to an optical axis of the image acquisition device, have been known (for example, see Japanese Unexamined Patent Application, Publication No. Hei 10-288742, Japanese Unexamined Patent Application, Publication No. 2007-216054, and Japanese Unexamined Patent Application, Publication No. 2005-74015).

BRIEF SUMMARY OF THE INVENTION

An object of the present invention is to provide an endoscope that is capable of improving the ease of insertion by reducing the size of a distal end of an inserted portion, while ensuring a preferable observation field of view by improving the light distribution of illumination light.

The present invention employs an endoscope that includes a tube-like inserted portion having a distal end; a light guiding member that is accommodated in the inserted portion and guides illumination light to the distal end; and an illumination optical system that radiates the illumination light guided by the light guiding member and an objective optical system that collects light from a region illuminated by the illumination optical system, which are disposed at the distal end of the inserted portion, wherein an end portion of the light guiding member facing the illumination optical system extends substantially parallel to an optical axis of the objective optical system, and a shoulder portion of the distal end and an outer surface of the illumination optical system located at the shoulder portion are inclined so as to become narrower toward the tip.

With the present invention, because the shoulder portion of the distal end of the inserted portion and the outer surface of the illumination optical system located at the shoulder portion are inclined so as to become narrower toward the tip, the ease of insertion into a body cavity, the interior of machinery, etc. can be improved. In addition, because the outer surface of the illumination optical system, such as a concave lens or the like, is inclined so as to become narrower toward the tip, the illumination light guided by the light guiding member can be radiated while being refracted toward the optical axis of the objective optical system, such as an objective lens or the like. Accordingly, with a preferable observation field of view being ensured, an illuminated region can be observed with the objective optical system, thereby making it possible to improve the observation precision thereof.

In the above-described invention, at least the distal end of the inserted portion and the illumination optical system may be integrally molded by double-shot molding using non-transparent plastic and transparent plastic.

By integrally molding the distal end of the inserted portion and the illumination optical system by double-shot molding, it is possible to eliminate the need to provide flanges in the distal end of the inserted portion for improving the ease of assembly of the illumination optical system. Accordingly, it is possible to reduce the size of the tip of the inserted portion and to make the tip shape thereof streamlined without protrusions, thereby making it possible to improve the ease of insertion into a body cavity, the interior of machinery, etc.

In the above-described invention, two of the illumination optical system may be provided and the two illumination optical systems may be disposed at positions that are substantially mirror symmetrical relative to a plane that passes through an optical axis of the objective optical system.

By doing so, the illumination light from the two illumination optical systems can be evenly radiated toward the optical axis of the objective optical system, thereby making it possible to ensure a preferable observation field of view.

In the above-described invention, when viewed from an optical axis direction of the objective optical system, an angle formed between the inclination direction at substantially the center of the outer surface of the illumination optical system and a diagonal direction of an observation field of view of the objective optical system may be 30° or less.

By doing so, the illumination light from the illumination optical system can be efficiently radiated toward the optical axis of the objective optical system, thereby making it possible to ensure a preferable viewing field for observation.

In the above-described invention, when viewed from the optical axis direction of the objective optical system, an angle formed between the inclination direction at substantially the center of the outer surface of the illumination optical system and a straight line that passes through the center of the objective optical system and the center of the illumination optical system may be 30° or less.

By doing so, the illumination light from the illumination optical system can be efficiently radiated toward the optical axis of the objective optical system, thereby making it possible to ensure a preferable observation field of view.

In the above-described invention, the illumination optical system may be a plano-concave lens in which an outer surface is formed of a flat surface and an inner surface is formed of a curved surface, and, in the plano-concave lens, at substantially the center of the outer surface of the illumination optical system, the curvature of the curved surface in the inclination direction may be formed larger than the curvature of the curved surface in a direction orthogonal to the inclination.

By doing so, the illumination light from the illumination optical system can be radiated toward the optical axis of the objective optical system with a large spread, thereby making it possible to efficiently illuminate the observation field of view; therefore, a preferable observation field of view can be ensured.

In the above-described invention, the illumination optical system may have a protrusion, which protrudes in a circumferential direction, on an inner surface side thereof, and the inserted portion may have a recess or a stepped portion that fits with the protrusion.

By doing so, the illumination optical system can be positioned with a simple structure without increasing the outside diameter of the scope tip. In addition, in the case of double-shot molding, the joining strength of the two types of plastics can be increased. Accordingly, the size of the tip of the inserted portion can be reduced by eliminating the need to provide the flanges in the inserted portion, thereby making it possible to improve the ease of insertion into the body cavity, the interior of machinery, etc.

With the present invention, an advantage is afforded in that the ease of insertion can be improved by reducing the size of a distal end of an inserted portion, while ensuring a preferable observation field of view by improving the light distribution of illumination light.

DETAILED DESCRIPTION OF THE INVENTION

An endoscope according to an embodiment of the present invention will be described below with reference to the drawings.

The endoscope 1 according to this embodiment is provided with, as main constituent components, an inserted portion 13 that has a tube-like shape and is inserted inside a body cavity, inside a machine, etc. to obtain internal images, a light-source device (not shown) that introduces illumination light into the inserted portion 13, an image processor (not shown) that applies image processing to the images obtained by the inserted portion 13, and a display unit (not shown) that displays image-processed images.

Figure 1:
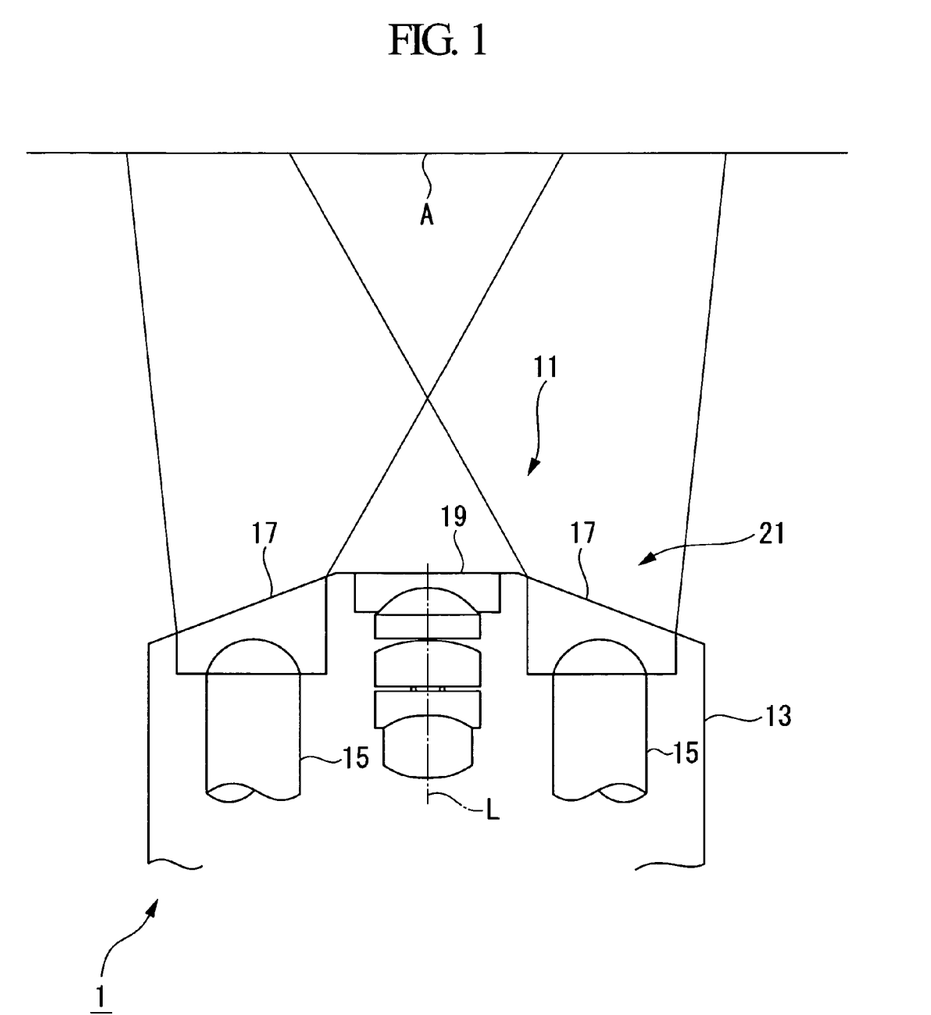
FIG. 1 is a schematic view of an endoscope according to an embodiment of the present invention.

FIG. 1 is a schematic diagram showing, in outline, the configuration of the inserted portion 13 according to this embodiment.

As shown in FIG. 1, the inserted portion 13 is provided with light guides (light guiding members) 15, which are accommodated in the inserted portion 13, an objective lens (objective optical system) 19 disposed at a distal end 11 of the inserted portion 13, and a pair of plano-concave lenses (illumination optical systems) 17 that are disposed radially outward of the objective lens 19 at the distal end 11 of the inserted portion 13. In addition, a shoulder portion 21 is formed at the distal end 11 of the inserted portion 13, and the shoulder portion 21 is inclined so as to become narrower toward the tip.

The light guides 15 are, for example, optical fibers, and are connected at their proximal ends to the light-source device (not shown) so as to guide the illumination light, which is emitted from the light-source device and enters from the proximal ends, toward the distal end 11. End portions of the light guides 15 that face the plano-concave lenses 17 extend substantially parallel to an optical axis L of the objective lens 19.

The plano-concave lenses 17 are concave lenses that are formed of flat surfaces on their outer surfaces and curved surfaces on their inner surfaces and are configured to irradiate an observation region A, facing the distal end 11, by spreading the illumination light guided by the light guides 15.

The distal end 11 of the inserted portion 13 and the plano-concave lenses 17 is integrally formed by double-shot molding using non-transparent plastic and transparent plastic. Specifically, the planoconcave lenses 17 are formed so as to increase in thickness radially inward of the inserted portion 13 and so that outer surfaces located at the shoulder portion 21 are inclined to become narrower toward the tip thereof. Accordingly, as shown in FIG. 1, the illumination light guided by the light guides 15 is spread at the concave surfaces and is then radiated while being refracted toward the optical axis L of the objective lens 19.

The objective lens 19 is configured to collect light from the observation region A illuminated by the plano-concave lenses 17. The light collected by the objective lens 19 is imaged on an image-acquisition device (not shown) and is converted to an electrical signal, which is transmitted to the image processor (not shown).

In the axial direction of the inserted portion 13, the two plano-concave lenses 17 are provided at locations closer to the proximal end relative to the tip of the objective lens 19. This is because the objective lens 19 readily receives the surrounding light due to its wide viewing angle. That is, sometimes the illumination light from the two plano-concave lenses 17 directly enters the objective lens 19 to cause flaring in the observed image. In order to prevent this flaring, the two plano-concave lenses 17 are provided closer to the proximal end relative to the objective lens 19.

Figure 2:
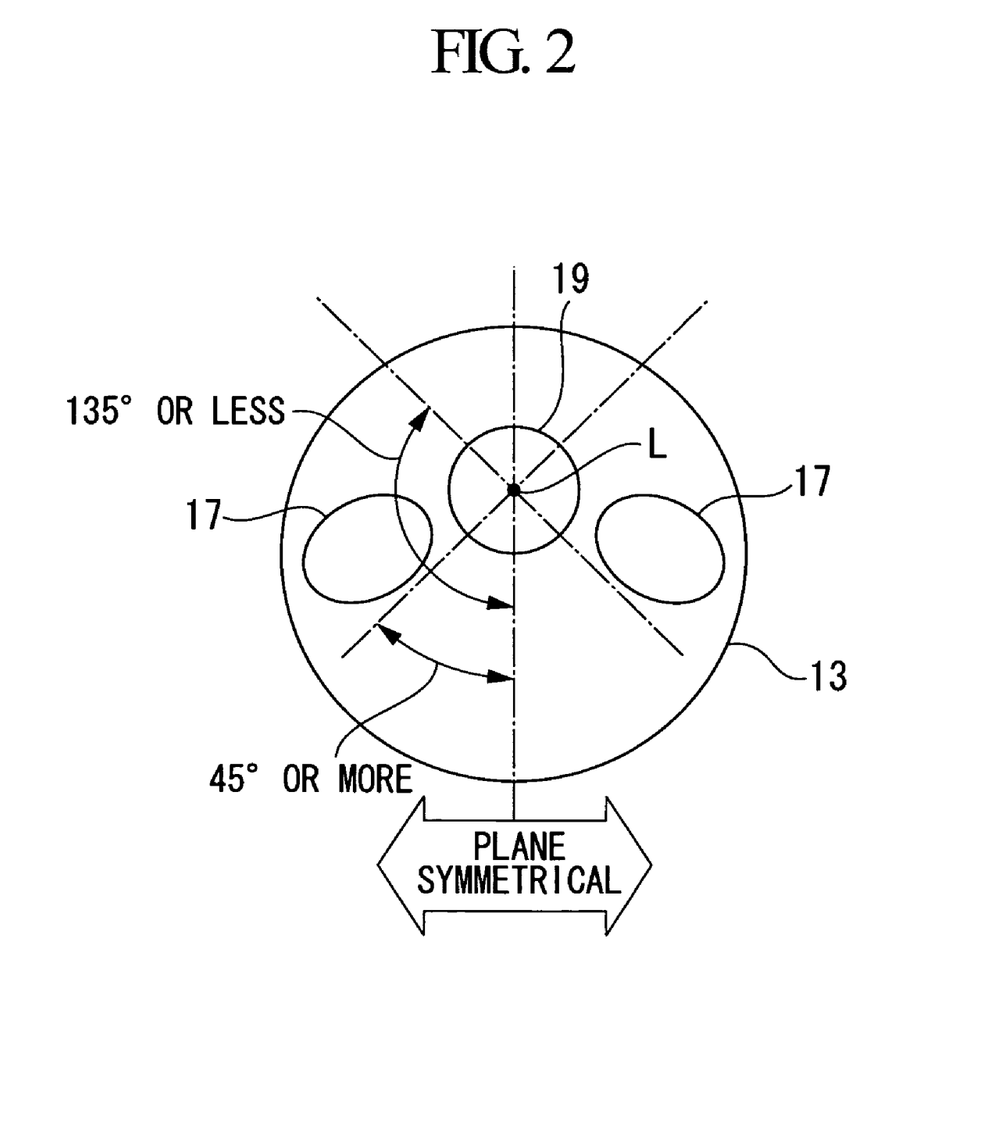
FIG. 2 is a front view of an inserted portion in FIG. 1, viewed from the tip side.

FIG. 2 is a front view of the inserted portion 13, viewed from the tip side.

As shown in FIG. 2, the objective lens 19 and the pair of plano-concave lenses 17 are provided at the distal end 11 of the inserted portion 13. Note that, although descriptions are omitted herein, in some cases, an instrument-insertion-channel opening (not shown), a water-pump nozzle for discharging water, and a front water-pump nozzle (not shown) for washing away blood, mucus, or the like, at an affected area of a subject, etc., are provided in the distal end 11 of the inserted portion 13 in addition to the objective lens 19 and the plano-concave lenses 17.

The pair of plano-concave lenses 17 are disposed in the distal end 11 of the inserted portion 13, centered on the optical axis L of the objective lens 19, so that the illumination intensity in the observation region is uniform. Specifically, the two plano-concave lenses 17 are disposed at positions that are substantially mirror symmetrical relative to a plane that passes through the optical axis L of the objective lens 19. In addition, when viewed from the tip side of the inserted portion 13, the two plano-concave lenses 17 are respectively disposed in a range between 45° and 135° and a range between −45° and −135° from symmetrical planes centered on the objective lens 19. Accordingly, even with small illumination means, the illumination distribution in the observation region is satisfactory, and at the same time, size reduction of the inserted portion 13 can be achieved.

Figure 3A:
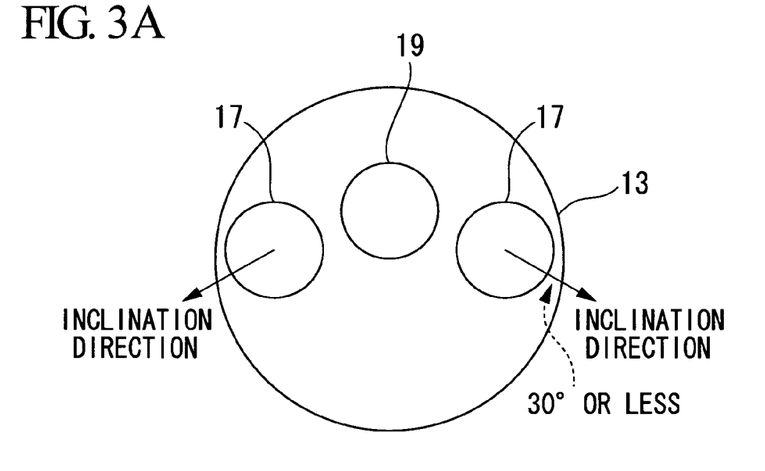
FIG. 3A is a diagram for explaining an inclination direction of a plano-concave lens in FIG. 1 and is a front view of the inserted portion, viewed from the tip side.
Figure 3B:
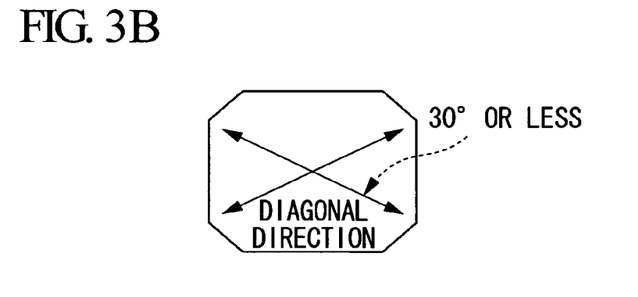
FIG. 3B is a diagram for explaining the inclination direction of the plano-concave lens in FIG. 1 and is a diagram showing an observation field of view.
Figure 3C:
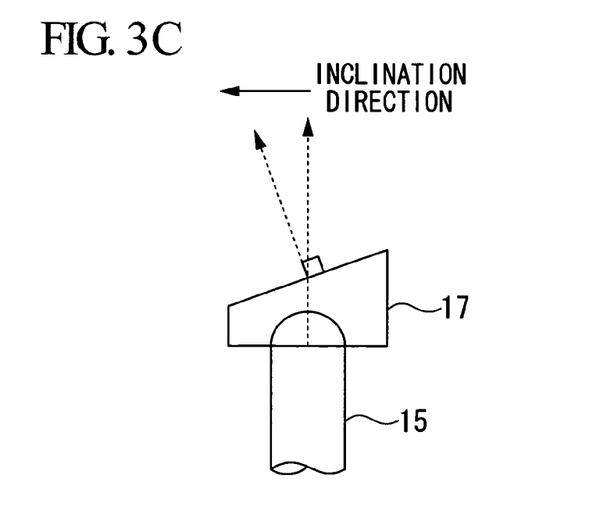
FIG. 3C is a diagram for explaining the inclination direction of the plano-concave lens in FIG. 1 and is a longitudinal sectional view in the inclination direction.

As shown in FIGS. 3A to 3C, the inclinations of the two plano-concave lenses 17 have defined directions. Here, FIG. 3A is a front view of the inserted portion 13, viewed from the tip side, FIG. 3B shows the observation field of view of the objective lens 19, and FIG. 3C is a longitudinal sectional view of a section defined by the inclination direction at substantially the center of the outer surface of plano-concave lenses 17 and the optical axis of the light guides 15.

Specifically, when viewed from the optical axis direction of the objective lens 19, the two plano-concave lenses 17 are configured so that an angle formed between the inclination directions at substantially the center of outer surfaces of the plano-concave lenses 17, i.e., the directions of arrows in FIGS. 3A and 3C, and the diagonal directions of the observation field of view of the objective lens 19, i.e., the directions of arrows in FIG. 3B, is 30° or less.

By doing so, the illumination light from the plano-concave lenses 17 can be efficiently radiated so that the illumination distribution in the observation region is satisfactory, when the observation distance is short as well as when it is long, thereby making it possible to ensure a preferable observation field of view.

The operation of the endoscope 1 having the above-described configuration will be described below.

Figure 7:
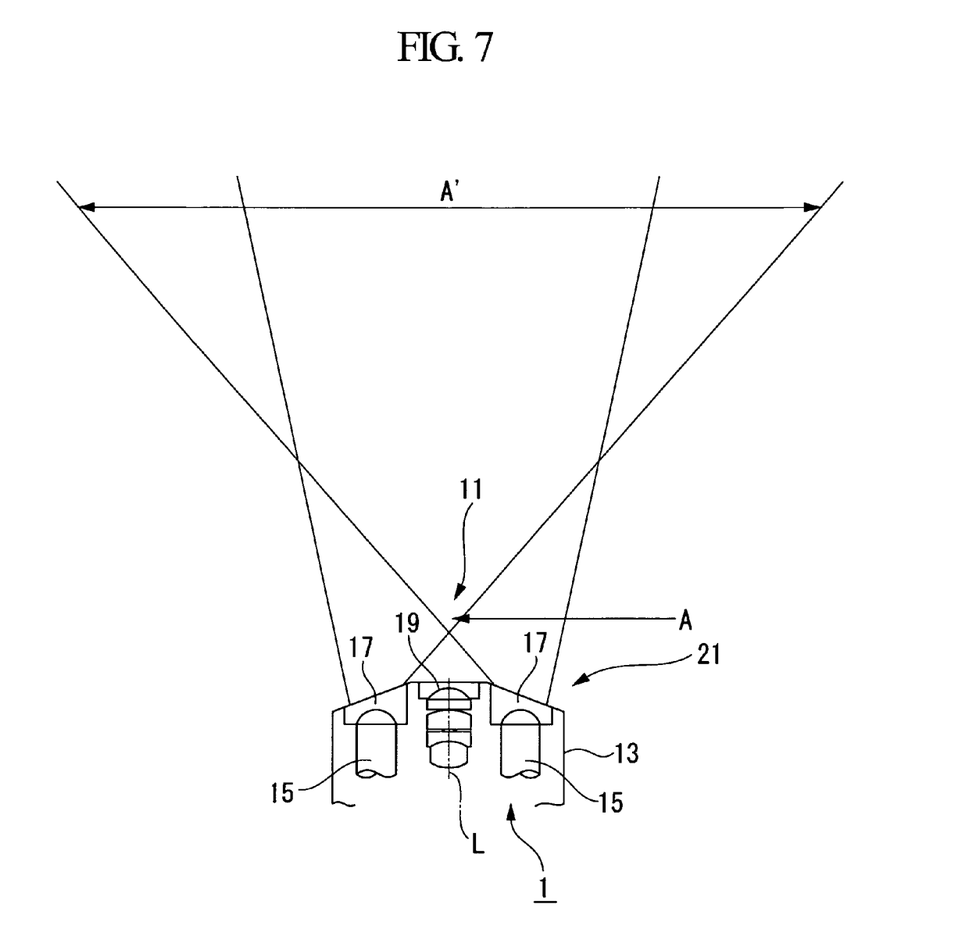
FIG. 7 is a diagram for explaining the operation of the endoscope in FIG. 1.

The illumination light emitted from the light source device (not shown) enters the proximal ends of the light guides 15, is internally reflected in the light guides 15, and is guided to the pair of plano-concave lenses 17 disposed at the distal end 11 of the inserted portion 13. The illumination light guided to the pair of plano-concave lenses 17, whose light rays are spread by the effects of the plano-concave lenses 17, is radiated while being refracted toward the optical axis L of the objective lens 19. Accordingly, the observation region A in the optical axis direction of the objective lens 19 is illuminated. At this time, because radiation directions of the plano-concave lenses 17 differ from each other, a region near the distal end 11 is illuminated well, as shown in FIG. 1, by overlapping the light from these lenses, and, in a region far from the distal end 11, a wide illumination area can be obtained, as shown in FIG. 7.

Reflected light from the observation region A is collected by the objective lens 19 and is imaged by the image acquisition device (not shown). Subsequently, the image is converted to an electrical signal to be subjected to image processing by the image processor, and an observation image is displayed on the display unit.

As a comparative example, illumination of the observation region A by a conventional endoscope will be described using FIG. 10.

Figure 10:
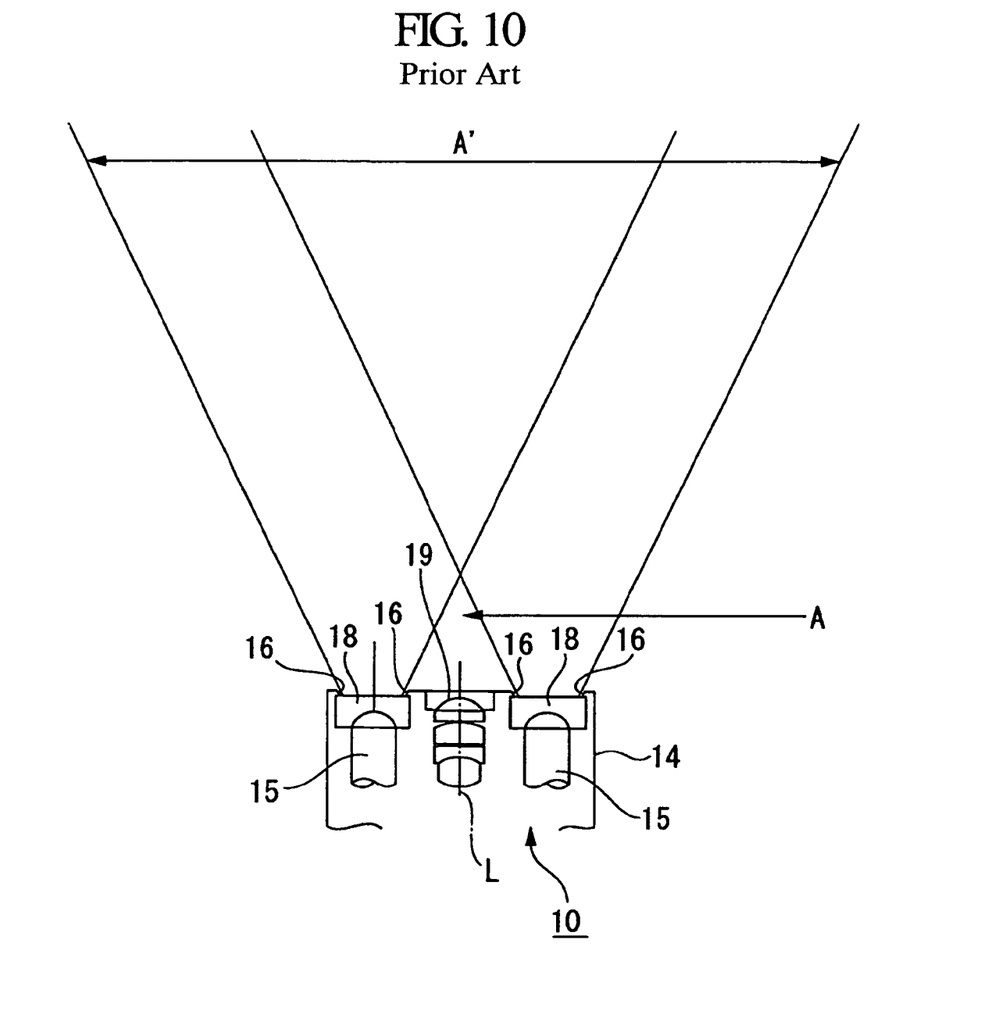
FIG. 10 is a schematic view of a conventional endoscope.

As shown in FIG. 10, with the conventional endoscope 10, illumination light from plano-concave lenses 18 is emitted parallel to the optical axis L of the objective lens 19; therefore, the observation region A cannot be illuminated well when the distance between a distal end of an inserted portion 14 and the observation region A is small. In addition, because the radiation directions of the individual plano-concave lenses 18 are the same, when the distance between the distal end and the observation region A is large, as shown in FIG. 10, an effect of widening the radiation region cannot be obtained.

Furthermore, in order to improve the ease of assembly, flanges 16 are provided at the distal end of the inserted portion 14. To prevent vignetting by these flanges 16, it is necessary to increase the outside diameters of the plano-concave lenses 18. As a result, the distal end of the inserted portion 14 inevitably increases in size, causing an inconvenience that the ease of insertion into the body cavity, the interior of machinery, etc., is impeded.

In contrast, with the endoscope 1 according to this embodiment, as shown in FIG. 7, because the shoulder portion 21 of the distal end 11 of the inserted portion 13 and the outer surfaces of the plano-concave lenses 17 located at the shoulder portion 21 are inclined so as to become narrower toward the tip, the ease of insertion into the body cavity, the interior of machinery, etc., can be improved. In addition, because the outer surfaces of the plano-concave lenses 17 are inclined to become narrower toward the tip, the illumination light guided by the light guiding members can be radiated while being refracted by the plano-concave lenses 17 toward the optical axis L of the objective lens 19. Accordingly, as shown in FIG. 7, the observation region A can be illuminated well when the distal end 11 of the inserted portion 13 is close to the observation region A. In addition, when the distal end 11 of the inserted portion 13 is far from the observation region A', an effect of widening the illuminated region is obtained, and thus, superior illumination can be extended to the peripheries. Therefore, the well-illuminated observation region A can be observed with the objective lens 19, and the observation precision thereof can be improved.

In addition, by integrally forming the distal end 11 of the inserted portion 13 and the plano-concave lenses 17 by double-shot molding, the need to provide the flanges for improving the ease of assembly of the plano-concave lenses 17 can be eliminated. Accordingly, it is possible to reduce the size of the distal end 11 of the inserted portion 13 and to make the tip shape thereof streamlined without protrusions, thereby making it possible to improve the ease of insertion into the body cavity, the interior of machinery, etc.

In addition, by disposing the two plano-concave lenses 17 at positions that are substantially mirror symmetrical relative to a plane that passes through the optical axis L of the objective lens 19, the illumination light from the two plano-concave lenses 17 can be evenly radiated toward the optical axis L of the objective lens 19, thereby making it possible to ensure a preferable observation field of view.

Furthermore, when the two plano-concave lenses 17 are viewed from the optical axis direction of the objective lens 19, by forming an angle of 30° or less between the inclination direction at substantially the center of the outer surfaces of the plano-concave lenses 17 and the diagonal direction of the observation field of view of the objective lens 19, the illumination light from the plano-concave lenses 17 can be efficiently radiated so that the illumination distribution in the observation region is satisfactory, when the observation distance is short as well as when it is long, thereby making it possible to ensure a preferable observation field of view.

First Modification

A first modification of the endoscope according to this embodiment will be described below.

Figure 4:
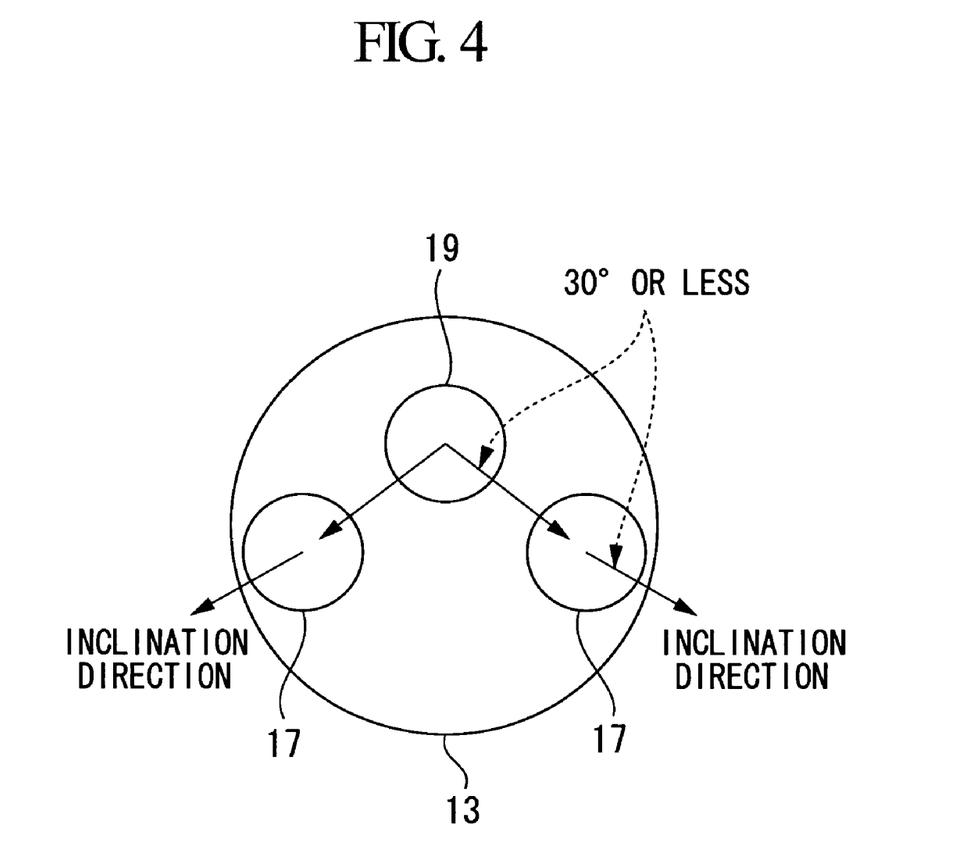
FIG. 4 is a front view of an inserted portion according to a first modification, viewed from the tip side.

As shown in FIG. 4, in an endoscope according to this modification, when viewed from the optical axis direction of the objective lens 19, an angle formed between the inclination direction at substantially the center of outer surfaces of the plano-concave lenses 17 and straight lines that pass through the center of the objective lens 19 and the centers of the plano-concave lenses 17 is 30° or less.

By doing so, the illumination light from the plano-concave lenses 17 can be efficiently radiated toward the optical axis L of the objective lens 19, thereby making it possible to ensure a preferable observation field of view.

Second Modification

Figure 5A:
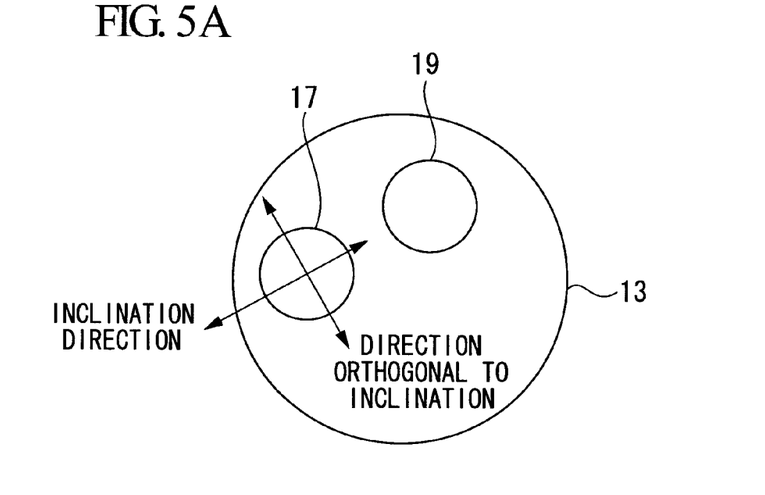
FIG. 5A is a diagram for explaining the shape of a curved surface of a plano-concave lens according to a second modification, and is a front view of an inserted portion, viewed from the tip side.
Figure 5B:
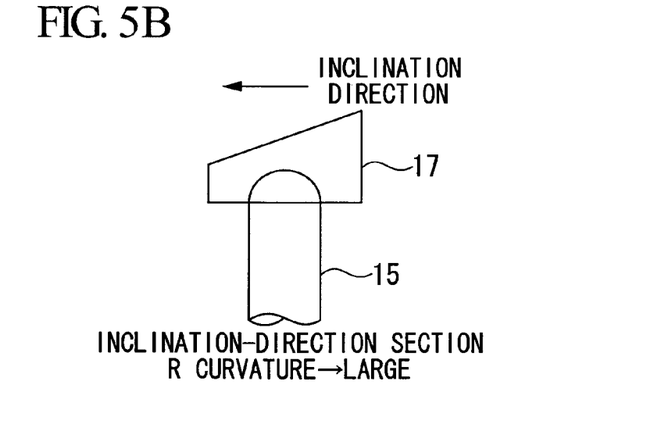
FIG. 5B is a diagram for explaining the shape of the curved surface of the plano-concave lens according to the second modification, and is a longitudinal sectional view in the inclination direction.
Figure 5C:
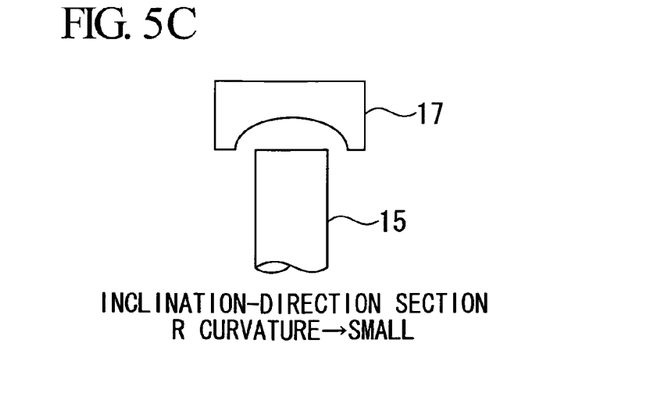
FIG. 5C is a diagram for explaining the shape of the curved surface of the plano-concave lens according to the second modification, and is a longitudinal sectional view in a direction orthogonal to the inclination.

As shown in FIGS. 5A to 5C, in a second modification of the endoscope according to this embodiment, the curvatures of the curved surfaces of the plano-concave lenses 17 may be changed. Here, FIG. 5A is a front view of the inserted portion 13 when viewed from the tip side thereof, FIG. 5B is a longitudinal sectional view of the plano-concave lens 17 in the inclination direction at substantially the center of the outer surface thereof, and FIG. 5C is a longitudinal sectional view of the plano-concave lens 17 in the direction orthogonal to the inclination thereof at substantially the center of the outer surface.

Specifically, the plano-concave lenses 17 are formed so that the curvatures of the curved surfaces in the inclination directions shown in FIG. 5B are larger than the curvatures of the curved surfaces in the direction orthogonal to the inclination direction shown in FIG. 5C, at substantially the center of the outer surfaces of the plano-concave lenses 17.

By doing so, the illumination light from the plano-concave lenses 17 can be radiated toward the optical axis L of the objective lens 19 with a large spread, and the observation region can be efficiently illuminated; therefore, it becomes possible to ensure a preferable observation field of view.

Third Modification

Figure 6:
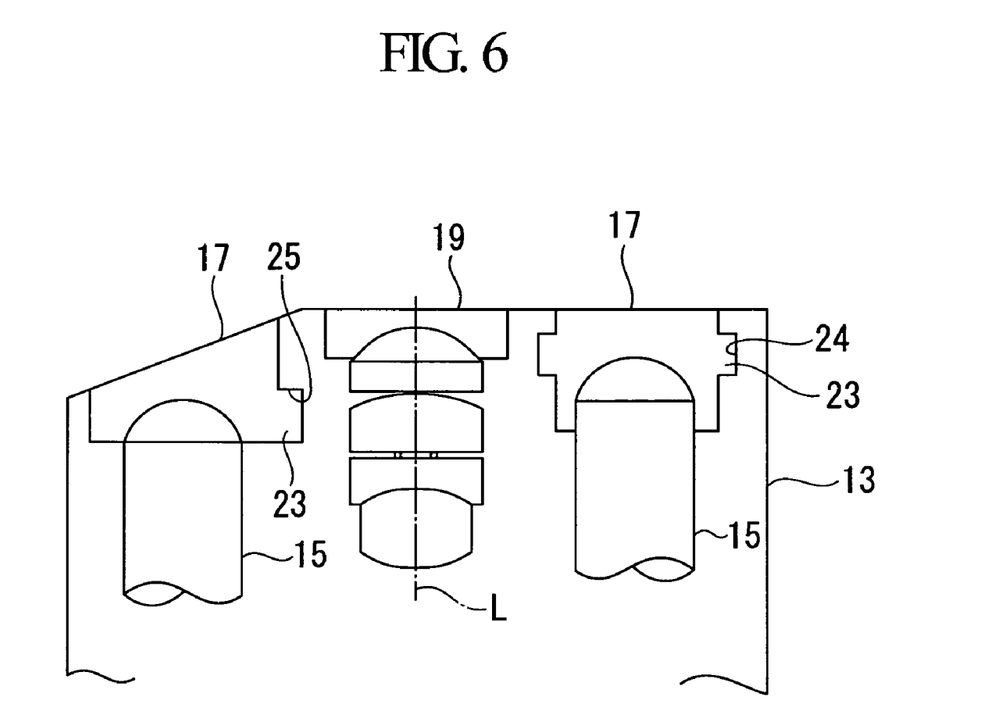
FIG. 6 is a schematic view of an endoscope according to a third modification.

As shown in FIG. 6, in a third modification of the endoscope according to this embodiment, the pair of plano-concave lenses 17 may have protrusions 23, which protrude in a circumferential direction, on an inner surface side thereof, and the inserted portion 13 may be provided with recesses 24 or stepped portions 25 that fit with the protrusions 23.

By doing so, the plano-concave lenses 17 can be easily positioned relative to the distal end 11 with a simple structure. In addition, in the case of double-shot molding, the joining strength of the two types of plastics can be increased. Accordingly, the size of the tip of the inserted portion 13 can be reduced by eliminating the need to provide the flanges in the inserted portion 13, thereby making it possible to improve the ease of insertion into the body cavity, the interior of machinery, etc.

Fourth Modification

Figure 8:
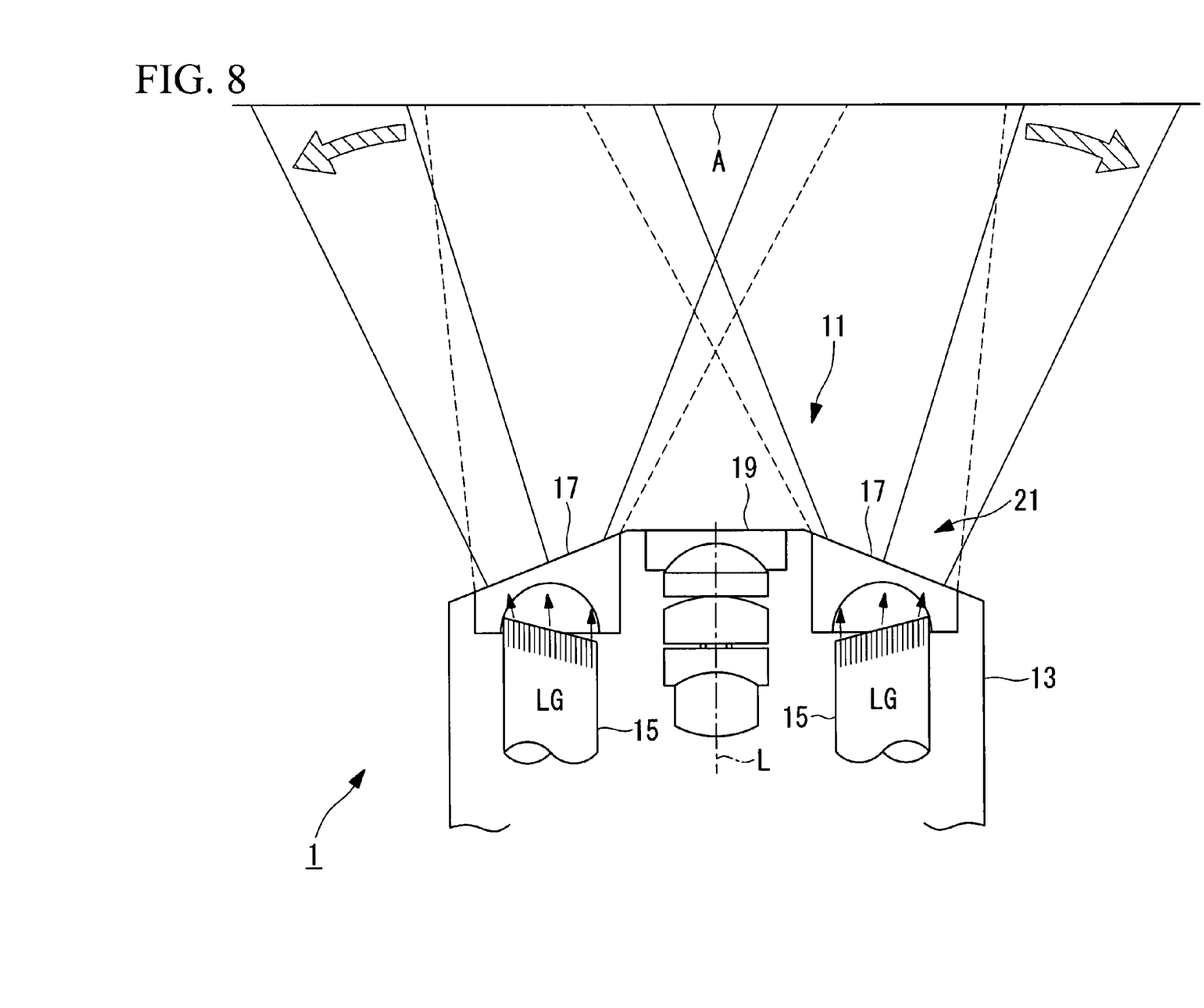
FIG. 8 is a schematic view of an endoscope according to a fourth modification.

As shown in FIG. 8, in a fourth modification of the endoscope according to this embodiment, end surfaces of the light guides 15 may be inclined in opposite directions from the inclination directions of the exit surfaces of the plano-concave lenses 17.

By doing so, the illumination light can be emitted in a direction such that it cancels out a reduction in the light distribution performance due to refraction at the inclined surfaces of the plano-concave lenses 17 by the refractive effect of the end surfaces of the light guides 15, which are inclined in the opposite directions in advance, thereby making it possible to improve the light distribution performance.

Fifth Modification

Figure 9:
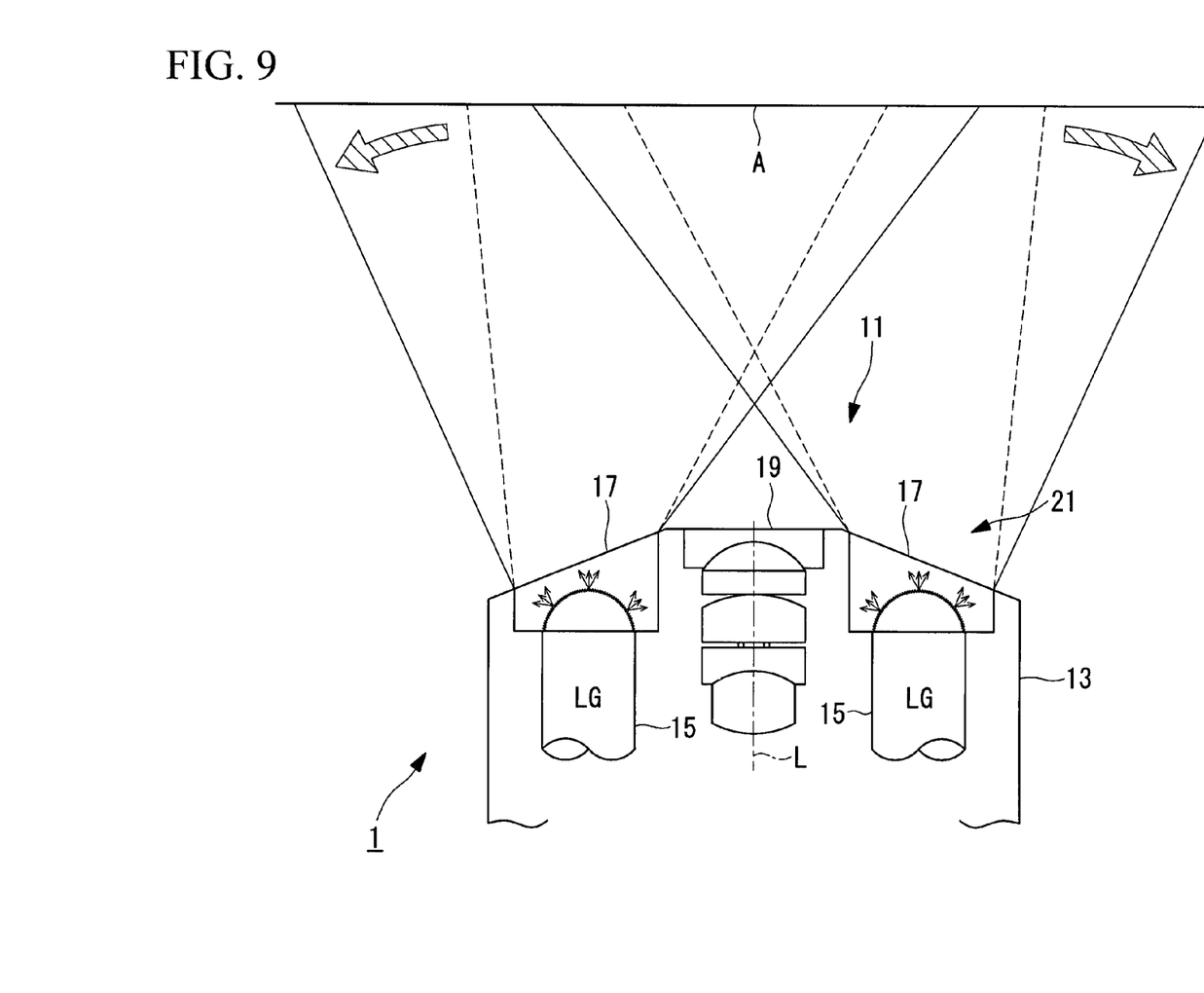
FIG. 9 is a schematic view of an endoscope according to a fifth modification.

As shown in FIG. 9, in a fifth modification of the endoscope according to this embodiment, light-diffusing surfaces (roughness) may be disposed on the concave surface sides of the plano-concave lenses 17.

By doing so, due the light-diffusing effects of the light-diffusing surfaces, the illumination light can be emitted in the direction that cancels out the reduction of the light-distribution performance due to the refraction at the inclined surfaces of the plano-concave lenses 17, thereby making it possible to improve the light-distribution performance.

The embodiment of the present invention has been described in detail above with reference to the drawings; however, specific configurations are not limited to this embodiment, and design alterations or the like that do not depart from the gist of the present invention are encompassed.

For example, although the descriptions assumed that two light guides 15 and two plano-concave lenses 17 are provided, three or more of each may be provided. In such a case, by disposing three or more plano-concave lenses 17 at positions that are substantially mirror symmetrical relative to a plane that passes through the optical axis L of the objective lens 19, the illumination light from the plano-concave lenses 17 can be evenly radiated toward the optical axis L of the objective lens 19, thereby making it possible to ensure a preferable observation field of view.

What is claimed is:

1. An endoscope comprising:
an image acquisition device for acquiring a subject image;
an objective optical system that has a predetermined optical axis along which the subject image is conveyed to the image-acquisition device;
a first light guiding member and a second light guiding member having exit surfaces that can emit illumination light along an optical axis which is parallel to the optical axis of the objective optical system;
a first optical system that is provided on the exit surface side of the first light guiding member and that refracts the optical axis of first illumination light, in the illumination direction thereof, along a diagonal direction of an observation field of view of the objective optical system so that the optical axis of the first illumination light emitted from the first light guiding member intersects with the optical axis of the objective optical system; and
a second optical system that is provided on the exit surface side of the second light guiding member and that refracts the optical axis of second illumination light, in the illumination direction thereof, along a diagonal direction of the observation field of view of the objective optical system so that the optical axis of the second illumination light emitted from the second light guiding member intersects with the optical axis of the objective optical system and also intersects with the optical axis of the first illumination light; and
a tube-like inserted portion having a distal end,
wherein the first optical system and the second optical system are disposed at the distal-end portion of the inserted portion and are also disposed at positions that are substantially mirror symmetrical relative to a plane that passes through the optical axis of the objective optical system; a shoulder portion of the distal end and the outer surfaces of the first optical system and the second optical system located at the shoulder portion are inclined so as to become narrower toward the tip; and, when viewed from the optical axis direction of the objective optical system, the inclination directions at substantially the center of the outer surfaces of the first optical system and the second optical system and straight lines that pass through the center of the objective optical system and the centers of the first optical system and the second optical system form angles of 30° or less.

2. An endoscope according to claim 1, wherein curvatures of curved surfaces of the first optical system and the second optical system in the inclination directions at substantially the centers of the outer surfaces of the first optical system and the second optical system are formed to be larger than curvatures of curved surfaces in directions orthogonal to the inclination directions.

3. An endoscope according to claim 1, wherein at least the distal end of the inserted portion is integrally molded with the first optical system and the second optical system by means of double-shot molding using non-transparent plastic and transparent plastic.

4. An endoscope according to claim 1, wherein, the first optical system and the second optical system have protrusions, which protrude in a circumferential direction, on an inner surface side thereof, and the inserted portion has recesses or stepped portions that fit with the protrusions.

* * * * *